US007326675B2

(12) United States Patent
Schneiderman et al.

(10) Patent No.: US 7,326,675 B2
(45) Date of Patent: Feb. 5, 2008

(54) HYDROPHOBICALLY MODIFIED POLYOLS FOR IMPROVED HYDROPHOBIC SOIL CLEANING

(75) Inventors: Eva Schneiderman, Mason, OH (US); Jun Ma, Beijing (CN); Kevin Todd Norwood, Cincinnati, OH (US); Fides Laura Rivera Permejo, Newcastle (GB); Randy Thomas Reilman, Cincinnati, OH (US); Julie Ann Menkhaus, Cleves, OH (US); Jeffrey John Scheibel, Loveland, OH (US)

(73) Assignee: Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/303,689

(22) Filed: Dec. 16, 2005

(65) Prior Publication Data

US 2006/0135396 A1  Jun. 22, 2006

Related U.S. Application Data

(60) Provisional application No. 60/637,204, filed on Dec. 17, 2004.

(51) Int. Cl.
*C11D 1/16* (2006.01)
*C11D 1/83* (2006.01)
*C11D 1/86* (2006.01)

(52) U.S. Cl. ............... 510/427; 510/235; 510/289; 510/290; 510/340; 510/351; 510/356; 510/504; 510/421; 510/422; 510/426; 510/428

(58) Field of Classification Search ............ 510/235, 510/289, 290, 340, 351, 356, 504, 421, 422, 510/426, 427, 428
See application file for complete search history.

(56) References Cited

U.S. PATENT DOCUMENTS

| | | | |
|---|---|---|---|
| 4,347,168 A | 8/1982 | Murphy et al. | |
| 4,661,288 A | 4/1987 | Rubingh et al. | |
| 4,746,456 A | 5/1988 | Kud et al. | |
| 4,814,102 A | 3/1989 | Baur et al. | |
| 4,846,994 A | 7/1989 | Kud et al. | |
| 4,849,126 A | 7/1989 | Kud et al. | |
| 4,904,408 A | 2/1990 | Kud et al. | |
| 4,906,397 A * | 3/1990 | Leighton et al. | ............ 510/361 |
| 4,908,150 A | 3/1990 | Hessel et al. | |
| 5,049,302 A | 9/1991 | Holland et al. | |
| 5,070,140 A | 12/1991 | Lind et al. | |
| 5,082,585 A | 1/1992 | Hessel et al. | |
| 5,156,906 A | 10/1992 | Holland | |
| 5,281,355 A * | 1/1994 | Tsaur et al. | .................. 510/393 |
| 5,318,719 A | 6/1994 | Hughes et al. | |
| 5,371,119 A | 12/1994 | Bohlander et al. | |
| 5,635,554 A | 6/1997 | Boeckh et al. | |
| 5,733,856 A | 3/1998 | Gopalkrishnan et al. | |
| 5,750,483 A | 5/1998 | Welch et al. | |
| 5,994,285 A * | 11/1999 | Sachdev et al. | ............ 510/329 |
| 5,998,357 A | 12/1999 | Appel et al. | |
| 6,083,488 A | 7/2000 | Riccobono et al. | |
| 6,159,918 A * | 12/2000 | Bae-Lee et al. | ............ 510/293 |
| 6,271,307 B1 | 8/2001 | Huff et al. | |
| 6,315,835 B1 | 11/2001 | Kerobo et al. | |
| 6,444,633 B2 | 9/2002 | Price | |
| 6,579,839 B2 | 6/2003 | Price et al. | |
| 6,579,953 B1 | 6/2003 | Gotsche et al. | |
| 2001/0036471 A1 | 11/2001 | Angel et al. | |
| 2003/0186833 A1 | 10/2003 | Huff et al. | |
| 2003/0224025 A1 | 12/2003 | Gotsche et al. | |
| 2004/0097657 A1 | 5/2004 | Morschhaeuser et al. | |
| 2005/0153860 A1* | 7/2005 | Zhou et al. | .................. 510/392 |
| 2005/0153867 A1* | 7/2005 | Scheibel et al. | ............ 510/499 |
| 2005/0170987 A1* | 8/2005 | Scheibel et al. | ............ 510/376 |
| 2005/0187133 A1* | 8/2005 | Schneiderman et al. | .... 510/475 |

FOREIGN PATENT DOCUMENTS

| | | |
|---|---|---|
| EP | 288067 | 10/1988 |
| EP | 325054 | 7/1989 |
| EP | 358474 | 3/1990 |
| EP | 0 377 916 A | 7/1990 |
| JP | 10-081744 | 3/1998 |
| JP | 10-140182 | 5/1998 |
| WO | WO 95/22593 | 8/1995 |
| WO | WO 01/05874 A1 | 1/2001 |
| WO | WO 01/79408 A1 | 10/2001 |
| WO | WO 01/98388 A1 | 12/2001 |
| WO | WO 02/11686 | 2/2002 |
| WO | WO 03/010256 | 2/2003 |
| WO | WO 2005/063847 A | 7/2005 |
| WO | WO 2005/078060 A | 8/2005 |

OTHER PUBLICATIONS

U.S. Appl. No. 10/661,317, filed Sep. 12, 2003, Ortiz et al, 2004/0068051A1.

(Continued)

*Primary Examiner*—Charles Boyer
(74) *Attorney, Agent, or Firm*—Stephen T. Murphy; Kim W. Zerby; Steve W. Miller

(57) ABSTRACT

Hydrophobically modified polyol compounds, compositions including the hydrophobically modified polyol compounds and methods of using such compositions and process of making such compositions for cleaning benefits.

16 Claims, No Drawings

OTHER PUBLICATIONS

U.S. Appl. No. 10/731,333, filed Dec. 9, 2003, Price et al, 2004/0121928A1.
U.S. Appl. No. 10/993,889, filed Nov. 21, 2004, Reddy et al, 2005/0113280A1.
U.S. Appl. No. 11/015,378, filed Dec. 17, 2004, Schneiderman et al, 2005/0187133A1.
U.S. Appl. No. 11/015,574, filed Dec. 17, 2004, Scheibel et al.
U.S. Appl. No. 11/015,575, filed Dec. 17, 2004, Scheibel et al, 2005/0153867A1.
U.S. Appl. No. 11/015,576, filed Dec. 17, 2004, Zhou et al, 2005/0153860A1.
U.S. Appl. No. 11/050,054, filed Feb. 3, 2005, Scheibel et al, 2005/0170987A1.
U.S. Appl. No. 11/083,649, filed Mar. 18, 2005, Song et al, 2005/0209125A1.
U.S. Appl. No. 11/300,714, filed Dec. 15, 2005, Carter et al.
U.S. Appl. No. 11/303,684, filed Dec. 15, 2005, Schneiderman et al.

* cited by examiner

HYDROPHOBICALLY MODIFIED POLYOLS FOR IMPROVED HYDROPHOBIC SOIL CLEANING

CROSS REFERENCE TO RELATED APPLICATION

This application claims priority under 35 U.S.C. § 119(e) to U.S. provisional application No. 60/637,204, filed Dec. 17, 2004.

FIELD OF THE INVENTION

The present invention relates to a composition having a hydrophobically modified polyol compound and a surfactant system for improved hydrophobic soil cleaning.

BACKGROUND OF THE INVENTION

Cleaning of hydrophobic soils such as grease and oil soils continues to be a challenge for detergent formulators, especially in regions where hand washing and/or colder water conditions exist. Many consumers in these regions may use hand washing process in addition to automating washing machines. The washing process in these regions will comprise the steps of soaking, pre-washing, pre-treating, and re-using of wash water. Often, wash water in the hand wash process is cold and may be high in impurities, such as hardness, concentration of transition metals and amounts of soil and particulates. All of these factors result in what is referred to as "stressed wash conditions", primarily in the amount of the soil, hardness, and particulates in the re-used wash water. These wash conditions are different from typical granular laundry detergents similar to those often found in the United States or the European Union via primary use of automatic washing machines.

Therefore, a problem associated with stressed wash conditions is the decreased level of hydrophobic soil cleaning due to the high soil, hardness and colder wash temperatures. Another problem associated with stressed wash conditions is the resulting graying of the white and light fabric items in the wash due to the deposition of the soil and particulates. Both problems are even more accentuated in the re-used wash water.

Known polymers for improved clay and hydrophilic soil cleaning and prevention of graying white and light fabric items in the wash include those polymers described in U.S. Pat. No. 4,661,288; U.S. Pat. No. 6,444,633; U.S. Pat. No. 6,579,839 and WO 01/05874. It is also known that some polymers can improve cleaning of other soils, such as those discussed in WO 01/79408 A1.

Polyol compounds such as sugar based materials are sustainable and readily available raw materials that lend themselves to be broadly tuned to address specific formulability and performance requirements. Specific performance requirements include providing cleaning of hydrophobic stains (grease, oil) under hand washing conditions having high soil and high hardness. Other performance requirements include use in automatic and hand-dishwashing compositions; surface cleaning compositions, such as floor cleaners, wood, ceramic tile, linoleum, cleaners; personal care compositions, such as shampoos, hair conditioners, soaps, body washes; and pet cleaning compositions.

Formulability of some of the current commercial polymers, which provide cleaning of grease and oil soils, into granular and liquid laundry detergents, hard surface cleaners, dish cleaning compositions and personal care compositions continues to challenge detergent formulators.

SUMMARY OF THE INVENTION

The present invention relates to a composition comprising: (a) one or more hydrophobically modified polyol compounds comprising from 5 to 11 hydroxy moieties, wherein at least one hydroxy moiety further comprises an alkoxy moiety selected from the group consisting of ethoxy, propoxy and mixtures thereof; wherein at least one of the hydroxy moieties, at least one alkoxy moiety, and combinations thereof, further comprise an anionic capping unit such that about 30% to 100% of the hydroxy moieties, alkoxy moiety, and combinations thereof comprise an anionic capping unit; and (b) a surfactant system comprising from about 9% to about 25% by weight of the composition of a $C_8$-$C_{18}$ linear alkyl benzene sulfonate and from 0% to about 7% by weight of the composition of a co-surfactant selected from nonionic surfactants, anionic surfactants, cationic surfactants, and mixtures thereof.

The present invention further relates to a process of making a composition comprising the steps of: (a) hydrophobically modifying a polyol compound wherein modification comprises having at least one hydroxy moiety of the polyol compound further comprising an ethoxy moiety and a propoxy moiety to form a hydrophobically modified polyol compound; (b) mixing the hydrophobically modified polyol compound with a surfactant system comprising from about 13% to about 25% by weight of the composition of $C_8$-$C_{18}$ linear alkyl benzene sulfonate and from 0% to about 7% by weight of the composition of a co-surfactant selected from nonionic surfactants, anionic surfactants, cationic surfactants, and mixtures thereof.

The present invention further relates to a method of using said composition. The present invention further relates to a hydrophobically modified polyol compound further described herein.

DETAILED DESCRIPTION OF THE INVENTION

There exists a need for compositions comprising materials that are relatively easy to manufacture from sustainable and readily available raw materials, which may be broadly tuned to address specific formulability and performance requirements. The selection of suitable materials is dependent upon the other components of the composition, performance requirements, processing requirements, washing conditions, and consumer habits involved in the use of the cleaning compositions.

Tunable polymers such as modified polyol compounds are believed to be agents that strengthen performance of detergent compositions and are believed to be effective in stressed wash conditions, in which surfactant alone is not capable of delivering desired hydrophobic soil cleaning, and at the same time effective in mitigating graying and yellowing of white fabrics. It should be noted however that the use of modified polyol compounds is not limited by stressed wash conditions, but modified polyol compounds may add to performance benefits in the non-stressed wash conditions.

It is believed, without being limited by a theory that the tunability of the polymer structure via modification of various molecular parameters in the system that enables use of the most suitable polymer for the desired application. Without being limited by a theory it is believed that the combination of the below described hydrophobically modified polyol compounds and below described surfactant systems enable interactions with hydrophobic soils and enables more efficient delivery of surfactant to surfaces being cleaned. In addition the modified polyol compounds alone, as well as in the mixture with below described surfactant systems, enable very efficient particulate soil dispersion further contributing to prevention of soil re-deposition.

As used herein "light-duty liquid dishwashing detergent composition" refers to those compositions that are employed in manual (i.e. hand) dishwashing. Such compositions are generally high sudsing or foaming in nature.

As used herein "laundry detergent composition" refers to those compositions that are employed in washing clothing and other fabrics in the automatic, semi-automatic, and/or hand washing and any solutions containing the composition in a diluted form.

As used herein "shampoo" refers to those compositions that are employed in washing of hair of human and animals.

As used herein "body wash" refers to those compositions in liquid form used for cleaning skin surfaces.

Incorporated and included herein, as if expressly written herein, are all ranges of numbers when written in a "from X to Y" or "from about X to about Y" or "X—Y" format. It should be understood that every limit given throughout this specification will include every lower or higher limit, as the case may be, as if such lower or higher limit was expressly written herein. Every range given throughout this specification will include every narrower range that falls within such broader range, as if such narrower ranges were all expressly written herein.

Unless otherwise indicated, weight percentage is in reference to weight percentage of the composition. All temperatures, unless otherwise indicated are in Celsius.

Hydrophobically Modified Polyol Compounds

As used herein "tune" means having the ability to manipulate the chemical structure of the polyol compounds to achieve distinguishing chemical functionality. For example, an alkoxylated modified polyol compound modified by further comprising an anionic capping unit is a tuned structure giving desired characteristics for specific formulability and performance requirements.

The modified polyol compounds useful in the present invention comprises from 5 to 11 hydroxy moieties, further 5 to 10 hydroxy moieties, further from 6 to 9 hydroxy moieties. Suitable polyol compounds for starting materials for use in the present invention include maltitol, sucrose, xylitol, pentaerythitol, glucose, maltose, matotriose, maltodextrin, maltopentose, maltohexose, isomaltulose, sorbitol, xylan, polyglycerol, diglycerol ether and mixtures thereof. Good examples include the polyol compound being selected as sorbitol, maltitol, and mixtures thereof.

At least one of the hydroxy moieties further comprising an alkoxy moiety, the alkoxy moiety is selected from ethoxy (EO) moieties, propoxy (PO) moieties and butoxy (BO) moieties, preferably a mixture of ethoxy (EO) moieties and propoxy (PO) moieties. The average degree of alkoxylation of individual hydroxyl moieties is from about 1 to about 100, preferably from about 4 to about 60, more preferably from about 10 to about 40. Alkoxylation is preferably block alkoxylation.

In one embodiment, block ethoxy and propoxy moieties comprise the alkoxy moiety. The average degree of ethoxylation is from 0 to 30, more preferably from 0 to 20, more preferably from about 2 to about 15, and even more preferably from 5 to 13. In one embodiment, the degree of propoxylation is preferably from about 2 to 60, more preferably from about 5 to 40, more preferably from about 5 to 30, and even more preferably from 8 to 20. In one embodiment, the modified polyol compound is preferably modified first propoxy units and then with ethoxy units.

The hydrophobically modified polyol compounds useful in the present invention further have at least one of the alkoxy moieties comprising at least one anionic capping unit. Suitable anionic capping unit include sulfate, sulfosuccinate, succinate, maleate, sulphonate, methylene carboxylate, ethylene carboxylate, phosphate, polyphosphate and mixtures thereof. Preferably the anionic capping units are sulfate and/or sulfonate. The amount of anionic capping units may range from 5% to 100%, more preferably from 30% to 100%, more preferably from 50% to 90%, more preferably from 60% to 80%, more preferably about 60% by available alkoxy moiety. For example, alkoxylated sorbitol has up to six alkoxy moieties that may have an anionic capping unit. In a non-limiting example, 60% of those 6 alkoxy moieties may comprise an anionic capping unit.

One embodiment comprises more than one hydroxy moiety further comprising an alkoxy moiety having an anionic capping unit. For example formula (I):

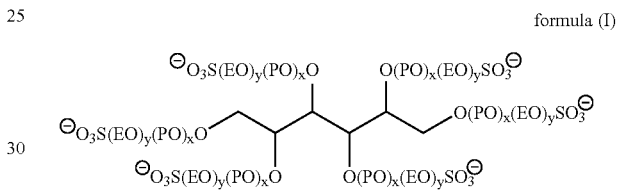

formula (I)

wherein x of formula (I) is an average from 0 to 30, or such as from 0 to 20, or such as from about 2 to 15, or such as from 5 to 13, y of formula (I) is an average from about 2 to 60, or such as from about 5 to 40, or such as from about 5 to 30, or such as from 8 to 20. Preferably formula (I) comprises 60-80% of anionic capping units on the available alkoxy moieties.

In general, a polyol is the unmodified "backbone" of the hydrophobically modified polyol compound discussed herein. The examples below in Table 1 may be similar to that for sorbitol such at that shown in formula (I) above with x and y of Table 1 being as defined above for formula (I).

TABLE 1 includes also "Mixtures of thereof"

| polyol | Average degree of propoxylation # PO/hydroxy moiety | Average degree of ethoxylation # EO/hydroxy moiety | # of sulfates[1]/ molecule (# of capping groups) |
|---|---|---|---|
| sorbitol | x | y | 0 |
| sorbitol | x | y | 1 |
| sorbitol | x | y | 2 |
| sorbitol | x | y | 3 |
| sorbitol | x | y | 4 |
| sorbitol | x | y | 5 |
| sorbitol | x | y | 6 |
| maltitol | x | y | 0 |
| maltitol | x | y | 1 |
| maltitol | x | y | 2 |
| maltitol | x | y | 3 |
| maltitol | x | y | 4 |
| maltitol | x | y | 5 |
| maltitol | x | y | 6 |
| maltitol | x | y | 7 |

TABLE 1-continued includes also "Mixtures of thereof"

| polyol | Average degree of propoxylation # PO/hydroxy moiety | Average degree of ethoxylation # EO/hydroxy moiety | # of sulfates[1]/ molecule (# of capping groups) |
|---|---|---|---|
| maltitol | x | y | 8 |
| maltitol | x | y | 9 |
| diglycerol | x | y | 0 |
| diglycerol | x | y | 1 |
| diglycerol | x | y | 2 |
| diglycerol | x | y | 3 |
| diglycerol | x | y | 4 |
| triglycerol | x | y | 1 |
| triglycerol | x | y | 2 |
| triglycerol | x | y | 3 |
| triglycerol | x | y | 4 |
| triglycerol | x | y | 5 |

[1]One of skill in the art will recognize that sulfate may be replaced by any suitable anionic capping unit discussed above.

One of skill will recognize that with less than 100% of the ethoxy moieties comprising anionic capping units, that materials with no anionic capping units will be present.

Process of Making

A process for making the modified polyol compound of the present invention comprises the optional step of alkoxylating a polyol compound comprising 5 to 11 hydroxy moieties such that the average degree of alkoxylation of at least one hydroxy moiety is between about 1 and about 100; and such as from about 4 to about 60; further such as from about 10 to about 40; to form an alkoxylated polyol comprising at least one alkoxy moiety. Alternatively, an alkoxylated polyol, such as CAS 52625-13-5, a propoxylated sorbitol or sorbitol polyoxy ethylene ether available from Lipo Chemicals Inc., may be used as the starting material. If the average degree of alkoxylation is not a desired level, an alkoxylation step may be used to achieve the desired degree of alkoxylation from about 1 to about 100, and such as from about 4 to about 60; further such as from about 10 to about 40. Next, the process comprises the step of reacting at least one alkoxy moiety of the compound with an anionic capping unit to form an anionic alkoxylated polyol, although more anionic capping units may be selected.

In one embodiment, the process comprises the step of alkoxylating some or most of the hydroxy moieties of the polyol such that the degree of alkoxylation is from about 1 to about 100; and such as from about 4 to about 60, further such as from about 10 to about 40; to form an alkoxylated polyol. The process further comprises the step of reacting the alkoxy moiety of the alkoxylated polyol with at least one anionic capping unit selected from one of the following anionic groups; sulfate, sulfonate, and mixtures thereof; to form an anionic alkoxylated polyol. The process may partially or completely react the alkoxy moiety of the alkoxylated polyol with an anionic capping unit. Preferably from 5% to 100%, 30% to 100%, 50%-90%, and 60% to 80% of the alkoxy moieties comprise an anionic capping unit. The sulfation process may be via use of chlosulfonic acid, falling film sulfur trioxide or via the addition of sulfuric acid as described in U.S. application Ser. No. 60/554576, filed Mar. 19, 2004, published as US 2005/0209476 A1.

Alkoxylation of Sorbitol

Propoxylation and ethoxylation of a polyol, such as sorbitol, or maltitol may be completed by any known technique, such as that described in EP 174436 A 1.

Add sorbitol (84.0 g, 0.4611 mol) to an autoclave, purge the autoclave with nitrogen, heat sorbitol to 110-120° C.; autoclave stirred and apply vacuum to about 267 Pa (20 mmHg).

Continuously apply vacuum while cooling the autoclave to about 110-120° C. and introducing 12.0 g of a 25% sodium methoxide in methanol solution (0.05553 moles, to achieve a 5% catalyst loading based upon hydroxy moieties). Remove the methanol from the methoxide solution and the autoclave under vacuum. Use a device to monitor the power consumed by the agitator. Monitor the agitator power along with the temperature and pressure. Agitator power and temperature values gradually increase as methanol is removed from the autoclave and the viscosity of the mixture increases and stabilizes in about 1.5 hours indicating that most of the methanol has been removed. The mixture is further heated and agitated under vacuum for an additional 30 minutes.

Remove the vacuum and cool the autoclave to or keep at 110-120° C. while charging with nitrogen to 1725 kPa (250 psia) and then vent to ambient pressure. Charge the autoclave to 1380 kPa (200 psia) with nitrogen. Propylene oxide (PO) may be added to the autoclave incrementally or in a single step while closely monitoring the autoclave pressure, temperature, and propylene oxide flow rate while maintaining the temperature between 110 and 120° C. and limiting any temperature increases due to reaction exotherm. A neutralization step with a sufficient amount of methane sulfonic acid (or other suitable neutralizing agents) may be used with the resulting basic form of the propoxylated sorbitol or the basic form may be stored under nitrogen gas for further tuning.

| Increment # | Starting reagent in grams (mol) | Grams PO | Moles PO | Target # PO/hydroxyl moiety | Neutralization with methane sulfonic acid |
|---|---|---|---|---|---|
| 1 | Sorbitol PO = 0; 84.00 g (0.4611) | 674.00 | 11.6047 | 4.2 | Yes: 1.188 g |
| 2 | Sorbitol PO = 4.2; 581.25 g (0.3536) | 715.00 | 12.3106 | 10 | No |

After the addition of 797.9 g (equivalent to 10 PO per each sorbitol hydroxy moiety) (0.2176 mol, resulting in a total of 10 moles of propylene oxide per mol of —OH (hydroxy moiety)), the temperature is increased to 120° C. and the mixture stirred for an additional 1.5 hours. Following propoxylation reaction, ethylene oxide (EO) is added to the autoclave incrementally while closely monitoring the autoclave pressure, temperature, and ethylene oxide flow rate while maintaining the temperature between 110 and 120° C. and limiting any temperature increases due to reaction exotherm. A neutralization step with a sufficient amount of methane sulfonic acid (or other suitable neutralizing agents) may be used with the resulting basic form of the propoxylated and ethoxylated sorbitol.

| Increment # | Starting reagent in grams (mol) | Grams EO | Moles EO | Target # EO/hydroxyl moiety | Neutralization with methane sulfonic acid |
|---|---|---|---|---|---|
| 1 | Sorbitol PO = 10; 797.9 g (0.2176) | 287.62 | 6.5153 | 5 | Yes: 0.61787 g |
| 2 | Sorbitol PO = 10; EO = 5; 807.76 g (0.1620) | 867.00 | 19.6822 | 25.2 | Yes: 1.46361 g |

After the incremental addition of 1154 g of ethylene oxide (25.1975 mol, resulting in a total of 25 moles of ethylene oxide (EO) per mol of —OH (hydroxy moiety)), the temperature is increased to 120° C. and the mixture stirred for an additional 1.5 hours.

The reaction mixture is then collected into a 5 L three neck round bottomed flask purged with nitrogen. The strong alkali catalyst is neutralized by slow addition of the indicated amount above of methane sulfonic acid with heating (110° C.) and mechanical stirring. The reaction mixture is then purged of residual ethylene oxide and deodorized by sparging an inert gas (argon or nitrogen) into the mixture through a gas dispersion frit while agitating and heating the mixture to 120° C. for 1 hour. The final reaction product, approximately 1306.90 g, is cooled slightly, and poured into a glass container purged with nitrogen for storage.

Alternatively, polyol may be purchased with a degree of alkoxylation that is at or below that desired, such as CAS 52625-13-5, a propoxylated sorbitol or sorbitol polyoxy ethylene ether available from Lipo Chemicals Inc. Wherein the desired degree of alkoxylation is achieved by the processes known and/or described above.

Sulfation of Sorbitol PO 60 EO 150 (Average of 10 PO and 25 EO Moieties Per Hydroxy Moiety)

Weigh into a 4L Erlenmeyer flask Sorbitol PO 60 EO 150 (800 g, 0.078 mol) and methylene chloride (800 g) ("the solution"). Equip the flask with a magnetic stirring bar and stir until complete dissolution. Place the flask in an ice bath until the solution reaches about 10° C. Stir vigorous while slowing pouring chlorosulfonic acid (62.5 g, 0.536 mol) over the period of about 10 minutes to form a reaction solution. Stir the reaction solution in the ice bath for 1.5 hours.

Place a solution of sodium methoxide (244 g of 25% in methanol) in 50 g of methylene chloride in a 1L Erlenmeyer flask ("base solution") and chill in an ice bath until the temperature of the solution reaches about 10° C. Stir the base solution vigorous using a magnetic stirring bar. Slowly pour the reaction solution into the base solution over a period of about 5 minutes. A mild exotherm should be observed. The resulting solution becomes milky as salts form. After addition is complete, measure the pH to be about 12. Pour the solution onto a large stainless steel tray with side shields, such that a very thin layer of solution is formed in the bottom. Place the tray in a fume hood and allow the solvent to evaporate at room temperature for 2 days to yield 900 g of off-white waxy solid, 92% active (8% salts).

Carbon NMR spectrum (500 MHz; pulse sequence: s2pu1, solvent $D_2O$; relax. delay 0.300 sec, pulse 45.0; acq. time 1.090 sec) shows an absence of alcohol groups at about 60 ppm and the emergence of a new peak at about 67 ppm consistent with formation of the end group sulfate. Proton NMR spectrum (500 MHz or 300 MHz; pulse sequence: s2pu1, solvent $D_2O$; relax. delay 1.000 sec, pulse 45.0; acq. time 2.345 sec) shows a new peak at about 4 ppm which was integrated against the ethoxy group protons at about 3.5 ppm and is consistent with the molecule having 6 end group sulfates.

Propoxylation and Ethoxylation of Maltitol 15PO 5EO 60% Sulfation

Ethoxylation of the polyol, such as maltitol may be completed by any known technique, such as that described in EP 174436 A1. Propoxylation may also be completed by known techniques.

Add maltitol (40.6 g, 0.118 mol) to a stirred autoclave followed by sodium methoxide (2.29 g of 25 wt % sodium methoxide in methanol solution (0.0106 mol sodium methoxide), to achieve an overall 9 mole % catalyst level, or 1 mole % per hydroxy moiety). Heat the maltitol mixture to 150° C. while applying vacuum 2.67-4 kPa (20-30 mmHg) to remove methanol. Stirring is applied once the mixture has melted and is agitated under vacuum for several hours (5-15 hours) until the methanol has been completely removed. The agitator power is monitored along with the temperature and pressure. Agitator power and temperature values gradually increase as methanol is removed from the autoclave and the viscosity of the mixture increases and stabilizes indicating that most of the methanol has been removed.

Add propylene oxide (PO) to the autoclave incrementally while closely monitoring the autoclave pressure and temperature while limiting any temperature increases due to reaction exotherm. A neutralization step with a sufficient amount of methanesulfonic acid (or other suitable neutralizing agents) may be used with the resulting basic form of the ethoxylated maltitol or the basic form may be stored under nitrogen gas for further tuning.

After the addition of 308.4 g of propylene oxide (5.31 mol, resulting in a total of 5 moles of propylene oxide per mole of hydroxy moiety (—OH)), the temperature is cooled to 135° C. before adding additional propylene oxide (615.6 g, 10.6 mol, resulting in a total of 15 propylene oxide per mole OH). Stir the mixture for 2 hours after all the propylene oxide has been consumed as indicated by no change in the pressure reading.

Cool the temperature to 120° C. and add ethylene oxide (EO) to the autoclave incrementally while closely monitoring the autoclave pressure and temperature while limiting any temperature increases due to reaction exotherm. Add 234 g of ethylene oxide (EO) (5.31 moles, resulting in a total of 5 moles of ethylene oxide per mole of hyroxy moiety (—OH)), and stir the mixture for 2 hours after all the ethylene oxide has been consumed as indicated by no change in the pressure reading. Cool the reaction mixture to 70° C. and collect into a glass jar, blanketed with nitrogen and sealed for storage Add to a 100 ml, single neck, round bottom flask Maltitol PO15 EO5 (16.5 g, 0.00162 mol) and methylene chloride (50 g). Equip the flask with a magnetic stir bar and water cooled condenser with argon inlet at top (attached to a bubbler). Mix under argon blanket until complete dissolution and add a solution of chlorosulfonic acid (1.57 g, 0.0135 mol) in 2-3 ml of methylene chloride and allow mixing over night (12-15 hours) at room temperature (20-25° C.).

Place the reaction mixture in a dropping funnel (with argon inlet at top). Attach the funnel to a 250 ml, single neck, round bottom flask containing 6.4 g of 25 wt % sodium methoxide solution in methanol (0.0296 mol sodium methoxide) and a magnetic stir bar. While chilling the flask with an ice water bath with good mixing, drip the reaction mixture into the methoxide solution. The resulting mixture will become milky as salts form. After addition is complete, measure the pH to insure it is alkaline. If not, add additional sodium methoxide solution. Attached the 250 ml flask to a rotary evaporator and concentrate the mixture by evaporating off methylene chloride. Dissolve the concentrate in 150 ml of deionized water and concentrate this mixture on a rotary evaporator to remove any traces of methylene chloride, methanol and some water to recover a clear, 20 wt % active aqueous solution. By $^1$H-NMR analysis, it is determined that approximately 60% of the alkoxy moieties are converted to sulfate groups.

Surfactant System

The composition of the present invention comprises a surfactant system comprising $C_8$-$C_{18}$ alkyl benzene sulfonates (LAS) and one or more co-surfactants selected from nonionic, cationic, anionic or mixtures thereof. The selection of co-surfactant may be dependent upon the desired benefit. In one embodiment, the co-surfactant is selected as a nonionic surfactant, preferably $C_{12}$-$C_{18}$ alkyl ethoxylates. In another embodiment, the co-surfactant is selected as an anionic surfactant, preferably $C_{10}$-$C_{18}$ alkyl alkoxy sulfates (AExS) wherein x is from 1-30. In another embodiment the co-surfactant is selected as a cationic surfactant, preferably dimethyl hydroxyethyl lauryl ammonium chloride.

The composition of the present invention further comprises from about from about 0.01% to about 90%, and such as from about 0.01% to about 80%, further such as from about 0.05% to about 50%, further such as from about 0.05% to about 40% by weight of the composition of a surfactant system.

$C_8$-$C_{18}$ Alkyl Benzene Sulfonates (LAS)

The surfactant system comprises from about 9% to about 25%, or from about 13% to about 25%, or from about 15% to about 23% by weight of the composition of $C_8$-$C_{18}$ alkyl benzene sulfonates (LAS). The surfactant system further comprises from 0% to about 7% or from about 0.1% to about 5%, or from about 1% to about 4% by weight of the composition of a co-surfactant selected from a nonionic co-surfactant, cationic co-surfactant, anionic co-surfactant and any mixture thereof.

Nonionic Co-Surfactants

Non-limiting examples of nonionic co-surfactants include: $C_{12}$-$C_{18}$ alkyl ethoxylates, such as, NEODOL® nonionic surfactants from Shell; $C_6$-$C_{12}$ alkyl phenol alkoxylates wherein the alkoxylate units are a mixture of ethyleneoxy and propyleneoxy units; $C_{12}$-$C_{18}$ alcohol and $C_6$-$C_{12}$ alkyl phenol condensates with ethylene oxide/propylene oxide block alkyl polyamine ethoxylates such as PLURONIC® from BASF; $C_{14}$-$C_{22}$ mid-chain branched alcohols, BA, as discussed in U.S. Pat. No. 6,150,322; $C_{14}$-$C_{22}$ mid-chain branched alkyl alkoxylates, BAE$_x$, wherein x is 1-30, as discussed in U.S. Pat. No. 6,153,577, U.S. Pat. No. 6,020,303 and U.S. Pat. No. 6,093,856; Alkylpolysaccharides as discussed in U.S. Pat. No. 4,565,647 Llenado, issued Jan. 26, 1986; specifically alkylpolyglycosides as discussed in U.S. Pat. No. 4,483,780 and U.S. Pat. No. 4,483,779; Polyhydroxy fatty acid amides (GS-base) as discussed in U.S. Pat. No. 5,332,528; and ether capped poly(oxyalkylated) alcohol surfactants as discussed in U.S. Pat. No. 6,482,994 and WO 01/42408.

Non-limiting examples of semi-polar nonionic co-surfactants include: water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms. See WO 01/32816, U.S. Pat. No. 4,681,704, and U.S. Pat. No. 4,133,779.

Nonionic co-surfactant, when present, may be present in an amount from 0.01% to about 4%, more preferably from about 0.1% to about 3%, more preferred, from about 0.5% to about 3% by weight of the composition.

Cationic Co-Surfactants

Non-limiting examples of cationic co-surfactants include: the quaternary ammonium surfactants, which can have up to 26 carbon atoms include: alkoxylate quaternary ammonium (AQA) surfactants as discussed in U.S. Pat. No. 6,136,769; dimethyl hydroxyethyl quaternary ammonium as discussed in U.S. Pat. No. 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260,529 and U.S. Pat. No. 6,022,844; and amino surfactants as discussed in U.S. Pat. No. 6,221,825 and WO 00/47708, specifically amido propyldimethyl amine (APA).

Cationic co-surfactant, when present, may be present in an amount from 0.01% to about 3%, more preferably from about 0.1% to about 3%, more preferably from about 0.1% to about 2% by weight of the composition.

Anionic Co-Surfactants

Nonlimiting examples of anionic co-surfactants useful herein include: $C_{10}$-$C_{20}$ primary, branched chain and random alkyl sulfates (AS); $C_{10}$-$C_{18}$ secondary (2,3) alkyl sulfates; $C_{10}$-$C_{18}$ alkyl alkoxy sulfates (AE$_x$S) wherein x is from 1-30; $C_{10}$-$C_{18}$ alkyl alkoxy carboxylates comprising 1-5 ethoxy units; mid-chain branched alkyl sulfates as discussed in U.S. Pat. No. 6,020,303 and U.S. Pat. No. 6,060,443; mid-chain branched alkyl alkoxy sulfates as discussed in U.S. Pat. No. 6,008,181 and U.S. Pat. No. 6,020,303; modified alkylbenzene sulfonate (MLAS) as discussed in WO 99/05243, WO 99/05242 and WO 99/05244; methyl ester sulfonate (MES); and alpha-olefin sulfonate (AOS).

Anionic co-surfactants, when present, may be present in an amount from about 0.01% to about 0.01% to about 5%, more preferable from about 0.1% to about 4%, more preferred about 1% to about 4% by weight of the composition.

Composition

The present invention relates to a composition comprising the modified alkoxylated polyol compound and a surfactant system comprising $C_8$-$C_{18}$ linear alkyl sulphonate surfactant and a co-surfactant. The compositions can be in any form, namely, in the form of a liquid, solid such as powder, granules, agglomerate, paste, tablet, pouches, bar, gel; emulsion; types delivered in dual-compartment containers, spray or foam detergents, premoistened wipes (i.e., the cleaning composition in combination with a nonwoven material such as that discussed in U.S. Pat. No. 6,121,165, Mackey, et al.), dry wipes (i.e., the cleaning composition in combination with a nonwoven materials, such as that discussed in U.S.

Pat. No. 5,980,931, Fowler, et al.) activated with water by a consumer, and other homogeneous or multiphase consumer cleaning product forms.

The compositions may be also suitable for use or incorporation into industrial cleaners (i.e. floor cleaners). In one embodiment, the cleaning composition of the present invention is a liquid or solid laundry detergent composition. In another embodiment, the cleaning composition of the present invention is a hard surface cleaning composition, preferably wherein the hard surface cleaning composition impregnates a nonwoven substrate. As used herein "impregnate" means that the hard surface cleaning composition is placed in contact with a nonwoven substrate such that at least a portion of the nonwoven substrate is penetrated by the hard surface cleaning composition, preferably the hard surface cleaning composition saturates the nonwoven substrate.

In another embodiment the cleaning composition is a liquid dish cleaning composition, such as liquid hand dishwashing compositions, solid automatic dishwashing cleaning compositions, liquid automatic dishwashing cleaning compositions, and tab/unit does forms of automatic dishwashing cleaning compositions.

The cleaning composition may also be utilized in car care compositions, for cleaning various surfaces such as hard wood, tile, ceramic, plastic, leather, metal, glass. This cleaning composition could be also designed to be used in a personal care composition such as shampoo composition, body wash, liquid or solid soap, pet care products and other cleaning composition in which surfactant comes into contact with free hardness and in all compositions that require hardness tolerant surfactant system, such as oil drilling compositions.

The composition may be made by a process comprising the steps of:

a) hydrophobically modifying a polyol compound wherein modification comprises having at least one hydroxy moiety of the polyol compound further comprising an ethoxy moiety and a propoxy moiety to form a hydrophobically modified polyol compound;

b) mixing the hydrophobically modified polyol compound with a surfactant system comprising from about 13% to about 25% by weight of the composition of $C_8$-$C_{18}$ linear alkyl benzene sulfonate and from 0% to about 7% by weight of the composition of a co-surfactant selected from nonionic surfactants, anionic surfactants, cationic surfactants, and mixtures thereof.

Further cleaning adjunct materials may be added in an optional step for the process. Hydrophobically modifying a polyol compound may be any tuning discussed above via the alkoxylation step and selecting an anionic capping unit.

Cleaning Adjunct Materials

In general, a cleaning adjunct is any material required to transform a composition containing only the minimum essential ingredients into a composition useful for laundry, hard surface, personal care, consumer, commercial and/or industrial cleaning purposes. In certain embodiments, cleaning adjuncts are easily recognizable to those of skill in the art as being absolutely characteristic of cleaning products, especially of cleaning products intended for direct use by a consumer in a domestic environment.

The precise nature of these additional components, and levels of incorporation thereof, will depend on the physical form of the cleaning composition and the nature of the cleaning operation for which it is to be used.

The cleaning adjunct ingredients if used with bleach should have good stability therewith. Certain embodiments of cleaning compositions herein should be boron-free and/or phosphate-free as required by legislation. Levels of cleaning adjuncts are from about 0.00001% to about 99.9%, and such as from about 0.0001% to about 50% by weight of the cleaning compositions. Use levels of the overall cleaning compositions can vary widely depending on the intended application, ranging for example from a few ppm in solution to so-called "direct application" of the neat cleaning composition to the surface to be cleaned.

Quite typically, cleaning compositions herein such as laundry detergents, laundry detergent additives, hard surface cleaners, synthetic and soap-based laundry bars, fabric softeners and fabric treatment liquids, solids and treatment articles of all kinds will require several adjuncts, though certain simply formulated products, such as bleach additives, may require only, for example, an oxygen bleaching agent and a surfactant as described herein. A comprehensive list of suitable laundry or cleaning adjunct materials can be found in WO 99/05242.

Common cleaning adjuncts include builders, enzymes, polymers not discussed above, bleaches, bleach activators, catalytic materials and the like excluding any materials already defined hereinabove. Other cleaning adjuncts herein can include suds boosters, suds suppressors (antifoams) and the like, diverse active ingredients or specialized materials such as dispersant polymers (e.g., from BASF Corp. or Rohm & Haas) other than those described above, color speckles, silvercare, anti-tarnish and/or anti-corrosion agents, dyes, fillers, germicides, alkalinity sources, hydrotropes, anti-oxidants, enzyme stabilizing agents, pro-perfumes, perfumes, solubilizing agents, carriers, processing aids, pigments, and, for liquid formulations, solvents, chelating agents, dye transfer inhibiting agents, dispersants, brighteners, suds suppressors, dyes, structure elasticizing agents, fabric softeners, anti-abrasion agents, hydrotropes, processing aids, and other fabric care agents, surface and skin care agents. Suitable examples of such other cleaning adjuncts and levels of use are found in U.S. Pat. Nos. 5,576,282, 6,306,812 B1 and 6,326,348 B1.

Method of Use

The present invention includes a method for cleaning a targeted surface. As used herein "targeted surface" may include such surfaces such as fabric, dishes, glasses, and other cooking surfaces, hard surfaces, hair or skin. As used herein "hard surface" includes hard surfaces being found in a typical home such as hard wood, tile, ceramic, plastic, leather, metal, glass. Such method includes the steps of contacting the composition comprising the modified polyol compound, in neat form or diluted in wash liquor, with at least a portion of a targeted surface then optionally rinsing the targeted surface. Preferably the targeted surface is subjected to a washing step prior to the aforementioned optional rinsing step. For purposes of the present invention, washing includes, but is not limited to, scrubbing, wiping and mechanical agitation.

As will be appreciated by one skilled in the art, the cleaning compositions of the present invention are ideally suited for use in home care (hard surface cleaning compositions), personal care and/or laundry applications.

The composition solution pH is chosen to be the most complimentary to a target surface to be cleaned spanning broad range of pH, from about 5 to about 11. For personal care such as skin and hair cleaning pH of such composition preferably has a pH from about 5 to about 8 for laundry cleaning compositions pH of from about 8 to about 10. The compositions are preferably employed at concentrations of from about 200 ppm to about 10,000 ppm in solution. The water temperatures preferably range from about 5° C. to about 100° C.

For use in laundry cleaning compositions, the compositions are preferably employed at concentrations from about 200 ppm to about 10000 ppm in solution (or wash liquor). The water temperatures preferably range from about 5° C. to about 60° C. The water to fabric ratio is preferably from about 1:1 to about 20:1.

The method may include the step of contacting a nonwoven substrate impregnated with an embodiment of the composition of the present invention. As used herein "nonwoven substrate" can comprise any conventionally fashioned nonwoven sheet or web having suitable basis weight, caliper (thickness), absorbency and strength characteristics. Examples of suitable commercially available nonwoven substrates include those marketed under the tradename SONTARA® by DuPont and POLYWEB® by James River Corp.

As will be appreciated by one skilled in the art, the cleaning compositions of the present invention are ideally suited for use in liquid dish cleaning compositions. The method for using a liquid dish composition of the present invention comprises the steps of contacting soiled dishes with an effective amount, typically from about 0.5 ml. to about 20 ml. (per 25 dishes being treated) of the liquid dish cleaning composition of the present invention diluted in water.

Formulations

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising:
a) one or more hydrophobically modified polyol compounds comprising from 5 to 11 hydroxy moieties, wherein at least one hydroxy moiety further comprises an alkoxy moiety selected from the group consisting of ethoxy, propoxy, butoxy and mixtures thereof; wherein at least one of the hydroxy moieties, at least one alkoxy moiety, and combinations thereof, further comprise an anionic capping unit such that about 5% to 100% of the hydroxy moieties, at least one alkoxy moiety, and combinations thereof, comprise an anionic capping unit wherein the hydrophobically modified polyol compound is derived from maltitol, sucrose, xylitol, pentaerythritol, glucose, maltose, matotriose, maltodextrin, maltopentose, maltohexose, isomaltulose, sorbitol, xylan, polyglycerol, diglycerol ether and mixtures thereof;
b) a surfactant system comprising from about 9% to about 25% by weight of the composition of a C8-C18 linear alkyl benzene sulfonate and from 0.01% to about 7% by weight of the composition of a co-surfactant selected from the group consisting of nonionic surfactants, cationic surfactants, and mixtures thereof;
wherein the nonionic surfactant is selected from the group consisting of C12-C18 alkyl ethoxylates; C6-C12 alkyl phenol alkoxylates, wherein the alkoxylate units are a mixture of ethyleneoxy and propyleneoxy units; C12-C18 alcohol and C6-C12 alkyl phenol condensates with ethylene oxide/propylene oxide block alkyl polyamine ethoxylates; C14-C22 mid-chain branched alcohols; C14-C22 mid-chain branched alkyl alkoxylates; alkylpolysaccharides; polyhydroxy fatty acid amides; ether capped poly(oxyalkylated) alcohol surfactants; water-soluble amine oxides containing one alkyl moiety of from about 10 to about 18 carbon atoms and 2 moieties selected from the group consisting of alkyl groups and hydroxyalkyl groups containing from about 1 to about

TABLE 2

Granular Laundry Detergent

| | A wt % | B wt % | C wt % | D wt % | E wt % |
|---|---|---|---|---|---|
| $C_{11-12}$ Linear alkyl benzene sulphonate | 13-25 | 13-25 | 13-25 | 13-25 | 9-25 |
| $C_{12-18}$ Ethoxylate Sulfate | — | — | 0-3 | — | 0-1 |
| $C_{14-15}$ alkyl ethoxylate (EO = 7) | 0-3 | 0-3 | — | 0-5 | 0-3 |
| Dimethyl hydroxyethyl lauryl ammonium chloride | — | — | 0-2 | 0-2 | 0-2 |
| Sodium tripolyphosphate | 20-40 | — | 18-33 | 12-22 | 0-15 |
| zeolite | 0-10 | 20-40 | 0-3 | — | — |
| silicate builder | 0-10 | 0-10 | 0-10 | 0-10 | 0-10 |
| Carbonate | 0-30 | 0-30 | 0-30 | 5-25 | 0-20 |
| diethylene triamine penta acetate | 0-1 | 0-1 | 0-1 | 0-1 | 0-1 |
| polyacrylate | 0-3 | 0-3 | 0-3 | 0-3 | 0-3 |
| Carboxy Methyl Cellulose | 0.2-0.8 | 0.2-0.8 | 0.2-0.8 | 0.2-0.8 | 0.2-0.8 |
| Polymer[1] | 1-5 | 1-5 | 1-5 | 1-5 | 1-5 |
| Percarbonate | 0-10 | 0-10 | 0-10 | 0-10 | 0-10 |
| nonanoyloxybenzenesulfonate | — | — | 0-2 | 0-2 | 0-2 |
| tetraacetylethylenediamine | — | — | 0-0.6 | 0-0.6 | 0-0.6 |
| Zinc Phthalocyanine Tetrasulfonate | — | — | 0-0.005 | 0-0.005 | 0-0.005 |
| Brightener | 0.05-0.2 | 0.05-0.2 | 0.05-0.2 | 0.05-0.2 | 0.05-0.2 |
| $MgSO_4$ | — | — | 0-0.5 | 0-0.5 | 0-0.5 |
| ENZYMES | 0-0.5 | 0-0.5 | 0-0.5 | 0-0.5 | 0-0.5 |
| MINORS (perfume, dyes, suds stabilizers) | balance | balance | balance | balance | balance |

[1]A polymer according to any one or mixture of the Examples from Table 1

3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms;

and wherein the cationic surfactant is selected from the group consisting of alkoxylate quaternary ammonium surfactants, dimethyl hydroxyethyl quaternary ammonium surfactant, dimethyl hydroxyethyl lauryl ammonium chloride; polyamine cationic surfactants, cationic ester surfactants, and amino surfactants, specifically amido propyldimethyl amine.

2. A composition of claim 1 wherein the modified polyol compound comprises from 5 to 10 hydroxy moieties.

3. A composition of claim 1 wherein the modified polyol compound comprises from 6 to 9 hydroxy moieties.

4. A composition of claim 3 wherein the alkoxy moiety comprises ethoxy and propoxy.

5. A composition of claim 1 wherein the anionic capping unit is selected from sulfate, sulfosuccinate, succinate, maleate, sulphonate, methylene carboxylate, ethylene carboxylate, phosphate, polyphosphate and mixtures thereof.

6. A composition of claim 5 wherein the anionic capping unit is selected from sulfate, sulfonate, methylene carboxylate and ethylene carboxylate.

7. A composition of claim 6 wherein the anionic capping units are such that 50% to 90% of the alkoxy moieties comprise an anionic capping unit.

8. A composition of claim 7 wherein the anionic capping units are such that 60% to 80% of the alkoxy moieties comprise an anionic capping unit.

9. A composition of claim 1 wherein the co-surfactant is selected as a nonionic surfactant.

10. A composition according to claim 1 further comprising an anionic co-surfactant.

11. A composition according to claim 1 wherein the co-surfactant is a cationic surfactant.

12. A composition of claim 10 wherein the anionic co-surfactant is selected from the group consisting of: $C_{10}$-$C_{20}$ primary, branched chain and random alkyl sulfates; $C_{10}$-$C_{18}$ secondary (2,3) alkyl sulfates; $C_{10}$-$C_{18}$ alkyl alkoxy sulfates; $C_{10}$-$C_{18}$ alkyl alkoxy carboxylates comprising 1-5 ethoxy units; mid-chain branched alkyl sulfates; mid-chain branched alkyl alkoxy sulfates; modified alkylbenzene sulfonate; methyl ester sulfonate; and alpha-olefin sulfonate.

13. A composition of claim 1 wherein the composition is in the form of a liquid detergent composition.

14. A composition of claim 1 wherein the composition is in the form of a solid detergent composition selected from the group consisting of powder, granules, agglomerate, paste, tablet, pouches, bar and gel.

15. A method of cleaning a targeted surface comprising the steps of identifying a targeted surface to be cleaned and contacting the composition of claim 1 with the targeted surface.

16. A process of making the composition of claim 1, comprising the steps of:
  a) hydrophobically modifying the polyol compound; and
  b) mixing the hydrophobically modified polyol compound with the surfactant system.

* * * * *

UNITED STATES PATENT AND TRADEMARK OFFICE
CERTIFICATE OF CORRECTION

PATENT NO. : 7,326,675 B2
APPLICATION NO. : 11/303689
DATED : February 5, 2008
INVENTOR(S) : Schneiderman et al.

Page 1 of 1

It is certified that error appears in the above-identified patent and that said Letters Patent is hereby corrected as shown below:

Title Page
After "( * )   Notice: Subject to any disclaimer, the term of this patent is extended or adjusted under 35 U.S.C. 154(b) by 0 days.", insert -- This patent is subject to a terminal disclaimer. --

Signed and Sealed this

Seventeenth Day of June, 2008

JON W. DUDAS
*Director of the United States Patent and Trademark Office*